United States Patent [19] [11] 4,148,890
Czok et al. [45] Apr. 10, 1979

[54] ANTIBIOTIC COMPOSITIONS FOR TREATING COCCIDIOSIS

[75] Inventors: Rudolf Czok, Mödling; Josef G. Meingassner, Vienna; Hubert Mieth, Wiener Neudorf; Eberhard Schütze, Vienna, all of Austria

[73] Assignee: Sandoz Ltd., Basel, Switzerland

[21] Appl. No.: 862,365

[22] Filed: Dec. 20, 1977

[30] Foreign Application Priority Data

Dec. 23, 1976 [CH] Switzerland .................. 16258/76

[51] Int. Cl.$^2$ .................. A61K 31/71; A61K 35/00; A61K 31/22
[52] U.S. Cl. .................. 424/181; 424/115; 424/116; 424/244; 424/246; 424/250; 424/270; 424/272; 424/273 R; 424/309; 424/311; 424/248.52; 424/248.55

[58] Field of Search ............... 424/115, 116, 248, 246, 424/244, 250, 270, 272, 273, 311, 181, 309

[56] References Cited
PUBLICATIONS

Chem. Abst. 9th Coll. Index vol. 76-85 (1972-1976) pp. 3115GS & 3116 GS.

Primary Examiner—Sam Rosen
Attorney, Agent, or Firm—Gerald D. Sharkin; Robert S. Honor; Thomas O. McGovern

[57] ABSTRACT

The invention provides a synergistic composition of a polyether antibiotic and a pleuromutilin derivative, which has an enhanced effect against coccidiosis in poultry. The composition may be prepared in the form of a premix concentrate and incorporated into commercial complete poultry feed. A method of treatment or prophylaxis of coccidiosis in poultry by co-administration of the components is also claimed.

10 Claims, No Drawings

ANTIBIOTIC COMPOSITIONS FOR TREATING COCCIDIOSIS

The invention relates to a combination of a pleuromutilin derivative and a polyether antibiotic, having an enhanced effect against poultry coccidiosis.

The invention provides a veterinary composition comprising a mixture of a compound of formula I

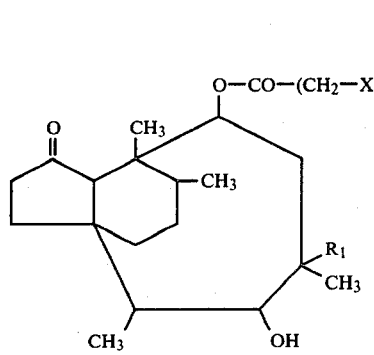

in which either
(1) $R_1$ is ethyl or vinyl
n is a whole number from 2 to 5
m is 0 or 1
X is —O—, —S— a group

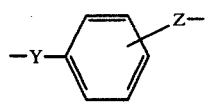

or a group —NR$_4$—
in which Y and Z either are both —S— or one is —S— and the other is —O—
and R$_4$ is hydrogen or a group of formula

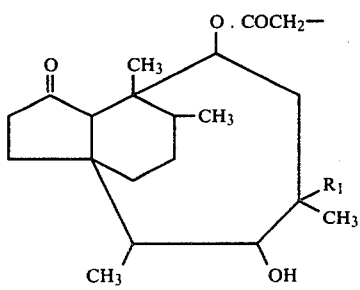

in which $R_1$ is as defined above,
and
$R_2$ and $R_3$ either
(a) are both alkyl, or
(b) together with the nitrogen atom form a heterocyclic ring which may contain as a further heteroatom —O—, —S— or a group —NR$_5$— in which R$_5$ is lower alkyl or lower hydroxyalkyl, or
(c) together with the nitrogen atom form a piperazinyl group in which the second nitrogen atom is substituted by a group R$_6$ in which R$_6$ is a lower alkyl group substituted by a lower acyloxy group, or is a lower benzoyloxyalkyl group,
or (2) $R_1$ is as defined above
n = 2
m = 1
$R_3$ is lower alkyl, lower hydroxyalkyl, lower alkyl substituted by a lower acyloxy group or lower benzyloxyalkyl,
X is —NR$_4$— and
$R_2$ together with $R_4$ forms an ethylene bridge between both nitrogen atoms,
with a polyether antibiotic selected from the group consisting of nigericin, grisorixin, salimonycin, dianemycin, septamycin, antibiotic A 204 A, laidlomycin, lysocellin, lonomycin, lasalocid A, B, C, D and E and monensin.

In the above definition of compounds of formula I, the word 'lower' means 'having from 1 to 6 carbon atoms'. The compounds of formula I have antibiotic properties, but on their own have no effect against coccidiosis. They are in part known and in part new.

The compounds of formula I$_a$

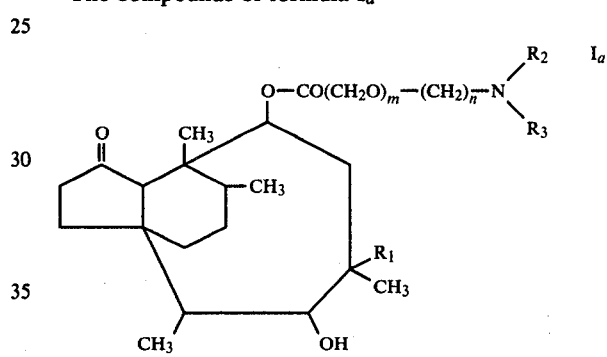

where n, m, $R_1$, $R_2$ and $R_3$ are as defined above, are new and can be obtained (i) by producing a compound of formula I$_a$ in which m = 1 by reacting a compound of formula II

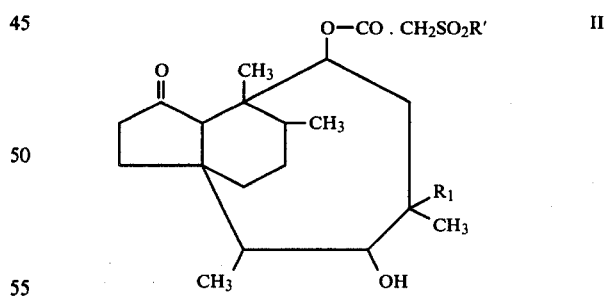

in which $R_1$ is as defined above and R' is an alkyl or aryl group, with a compound of formula III

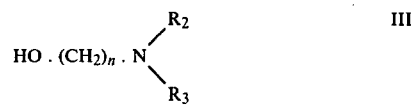

where n, $R_2$ and $R_3$ are as defined above, or
(ii) by producing a compound of formula I$_a$ in which m = 0 by reacting a compound of formula IV

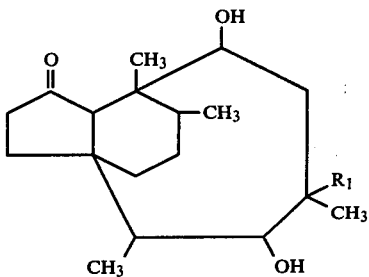

in which $R_1$ is as defined above, with a compound of formula V

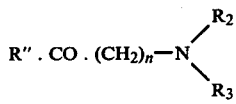

in which n, $R_2$ and $R_3$ are as defined above and R" is a halogen or an acyl group.

The above-named polyether antibiotics are known, and are known to have anti-coccidic properties. Their structural formulae are given in the literature, for example in Annual Reports in Medicinal Chemistry 10 [1975]: Chapter 25 "The Polyether Antibiotics," pp. 246–256, or in Experientia 32 p 319, 1976.

It has now been found that the efficacy of these polyether antibiotics against poultry coccidiosis is increased by the addition of a compound of formula I, so that an equivalent effect can be obtained by a reduced dose of polyether antibiotic administered together with a compound of formula I. As the compounds of formula I themselves have no anti-coccidic effect, this is attributable to a synergistic effect between the compounds of formula I and the above polyether antibiotics.

This may be demonstrated by experimental studies in day-old chicks infected with Eimeria tenella and given food containing polyether antibiotic alone (3-125 ppm) or in combination with a compound of formula I (3-125 ppm). The efficacy against coccidiosis is measured according to the efficacy index described in Poultry Science 56 (1977) pp. 1281–1288, based upon weight gain, mortality and the appearance and oocyte content of the droppings. A prophylactic effect can be demonstrated when the medicated foodstuff is given prior to infection.

Indicated suitable contents in feed are 12.5-125 ppm of polyether antibiotic and 3-125 ppm of compound of formula I.

The preferred compounds of formula I are those in which m is 1 or 0 and $R_1$, n, X, $R_2$ and $R_3$ are as defined above. Particularly preferred are those in which m is 1, X is —O—, —S— or a group

where Y and Z are as defined above, and n, $R_1$, $R_2$ and $R_3$ are as defined above. The most preferred compound of formula I is 14-desoxy-14[(2-diethylaminoethyl)-mercaptoacetoxy]mutilin (=tiamulin); that is, the compound of formula I in which m=1, n=2, X is —S—, $R_1$ is vinyl and $R_2$=$R_3$=ethyl.

The preferred polyether antibiotics are salinomycin, lasalocid, septamycin, monensin or antibiotic A 204 A. Particularly preferred combinations are those containing lasalocid and tiamulin or monensin and tiamulin.

The combination according to the invention may be produced in the form of a concentrate by mixing the two components in powder form, optionally together with a diluent, for example soya flour or corn starch, and this concentrate may then be added to the feed in the requisite amount.

A suitable ratio of polyether antibiotic to compound of formula I in the concentrate or in the feed is between 1:10 and 20:1, preferably 1:5 to 5:1, more preferably 2:3 to 3:2, particularly 1:1. Thus for a combination of lasalocid (normally administered in feed at a concentration of 75 ppm) and tiamulin, it is found that addition of 12.5 ppm tiamulin (L:T=5:1) gives improved results, and that a mixture of 125 ppm tiamulin with 2 ppm lasalocid (L:T=1:5) gives as good results as with 75 ppm lasalocid alone. A preferred combination in feed is 50 ppm lasalocid with 60 ppm tiamulin. For monensin, normally administered at 110 ppm, the results are significantly improved by the addition of 6 ppm tiamulin (M:T=18:1); and 125 ppm tiamulin with only 12.5 ppm monensin (M:T=1:10) gives as good results as 110 ppm monensin alone. A preferred combination in feed is 50 ppm monensin with 50 ppm tiamulin.

The two components of the combination may also be administered separately, for example the polyether antibiotic in the feed and the compound of formula I in the drinking water. In this way the normal dosage of polyether antibiotic may be supplemented by dosage with compound of formula I for a shorter period. A suitable treatment, for example, comprises continuous administration of lasalocid or monensin together with administration of tiamulin in drinking water for 2–3 days only. Suitable concentrations for this mode of administration are those described above for administration of both components in the feed.

The following Examples illustrate the invention:

EXAMPLE 1:

1 Kg monensin and 1 kg tiamulin are mixed together in powdered form with 18 kg soya flour, to give 20 kg of a premix concentrate containing 5% monensin and 5% tiamulin by weight.

1 Kg of the concentrate is mixed thoroughly with 1000 kg of commercial complete poultry feed, to give a feed containing 50 ppm monensin and 50 ppm tiamulin.

EXAMPLE 2:

1 Kg lasalocid and 1.2 kg tiamulin are mixed together in powdered form with 17.8 kg corn starch to give 20 kg of a premix concentrate containing 5% lasalocid and 6% tiamulin by weight.

1 Kg of the concentrate is mixed thoroughly with 1000 kg of commercial complete poultry feed, to give a feed containing 50 ppm lasalocid and 60 ppm tiamulin.

What is claimed is:

1. A veterinary composition for treating coccidiosis comprising in effective amounts a mixture of a compound of formula I

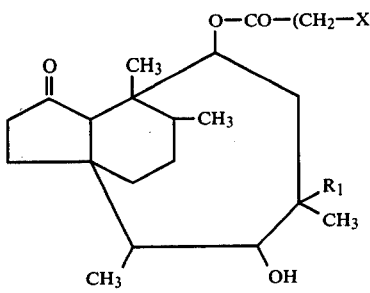

I n which either
(1) R₁ is ethyl or vinyl
n is a whole number from 2 to 5
m is 0 or 1
X is —O—, —S— a group

or a group —NR₄— in which Y and Z either are both —S— or one is —S— and the other is —O— and R₄ is hydrogen or a group of formula

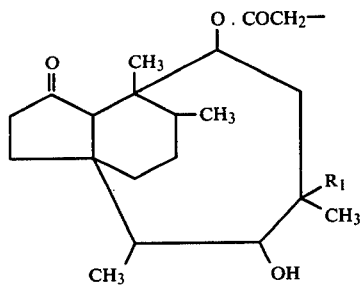

in which R₁ is as defined above,
and
R₂ and R₃ either
  (a) are both alkyl, or
  (b) together with the nitrogen atom form a heterocyclic ring which may contain as a further heteroatom —O—, —S— or a group —NR₅— in which R₅ is lower alkyl or lower hydroxyalkyl, or
  (c) together with the nitrogen atom form a piperazinyl group in which the second nitrogen atom is substituted by a group R₆ in which R₆ is a lower alkyl group substituted by a lower acyloxy group, or is a lower benzoyloxyalkyl group,
or
(2) R₁ is as defined above
n = 2
m = 1
R₃ is lower alkyl, lower hydroxyalkyl, lower alkyl substituted by a lower acyloxy group or lower benzoyloxyalkyl,
X is —NR₄—
and
R₂ together with R₄ forms an ethylene bridge between both nitrogen atoms,
with a polyether antibiotic selected from the group consisting of nigericin, grisorixin, salimonycin, dianemycin, septamycin, antibiotic A 204 A, laidlomycin, lysocellin, lonomycin, lasalocid, A, B, C, D and E and monensin.

2. A composition according to claim 1 in which the ratio of polyether antibiotic to compound of formula I lies between 1:10 and 20:1.

3. A composition according to claim 1 in which the compound of formula I is 14-desoxy-14[(2-diethylaminoethyl)-mercaptoacetoxy]mutilin (tiamulin).

4. A composition according to claim 1 in which the polyether antibiotic is lasalocid or monensin.

5. A composition according to claim 1 in the form of a concentrate consisting essentially of polyether antibiotic, compound of formula I and, a diluent.

6. A poultry feed comprising a composition according to claim 1.

7. A poultry feed according to claim 6 containing from 12.5 to 125 ppm of polyether antibiotic and 3 to 125 ppm of compound of formula I.

8. A method of prophylaxis or of treatment of coccidosis in poultry comprising co-administration of a polyether antibiotic listed in claim 1 with a compound of formula I, stated in claim 1.

9. A method according to claim 8 in which a mixture of polyether antibiotic and compound of formula I is administered in the feed.

10. A method according to claim 8 in which the polyether antibiotic is administered in the feed and the compound of formula I is administered in solution in the drinking water.

* * * * *